United States Patent
LeJeune

(10) Patent No.: US 6,267,232 B1
(45) Date of Patent: Jul. 31, 2001

(54) DISPOSABLE PATIENT GARMENT SYSTEM

(76) Inventor: Lori J. LeJeune, P.O. Box 1962, Warsaw, MO (US) 65355

( * ) Notice: Subject to any disclaimer, the term of this patent is extended or adjusted under 35 U.S.C. 154(b) by 0 days.

(21) Appl. No.: 09/286,506

(22) Filed: Apr. 6, 1999

(51) Int. Cl.⁷ .................................................. B65D 81/28
(52) U.S. Cl. .......................................... 206/213; 206/438
(58) Field of Search ................... 206/213, 278, 206/363, 438, 440, 38, 439

(56) References Cited

U.S. PATENT DOCUMENTS

| | | | |
|---|---|---|---|
| 3,096,148 | * | 7/1963 | Walker .............................. 206/213 |
| 3,494,726 | * | 2/1970 | Barasch ............................. 206/278 |
| 3,559,317 | * | 2/1971 | Knight et al. ..................... 206/213 |
| 3,967,728 | * | 7/1976 | Gordon et al. .................... 206/438 |
| 4,352,429 | * | 10/1982 | Newman ............................ 206/439 |
| 4,446,575 | | 5/1984 | Davis .................................... 2/400 |
| 4,930,161 | | 6/1990 | Cohen .................................... 2/114 |
| 4,951,815 | * | 8/1990 | Ulbrich .............................. 206/213 |
| 5,103,501 | | 4/1992 | Meisels ................................. 2/113 |
| 5,341,515 | | 8/1994 | Cohen .................................... 2/400 |
| 5,546,608 | | 8/1996 | Russano ................................ 2/408 |
| 5,548,859 | * | 8/1996 | Oberg et al. ...................... 206/213 |

* cited by examiner

Primary Examiner—David T. Fidei
(74) Attorney, Agent, or Firm—Joseph N. Breaux

(57) ABSTRACT

A disposable patient garment system that includes a disposable patient garment that is constructed in the general shape of elastic waisted shorts that can be worn while waiting to be examined but that have a split from the front center thereof down between the two legs and up the back side to the back center thereof to not hinder the examination. The system also includes a moisture proof packaging and disposal bag that is used to initially package and store the disposable patient garment and that includes a sealable lower garment holding chamber into which the used disposable patient garment is sealed with a two-part sealing mechanism after a rupturable disinfectant holding cell filled with an alcohol based disinfectant is ruptured to ensure safe disposal of the medical waste.

1 Claim, 3 Drawing Sheets

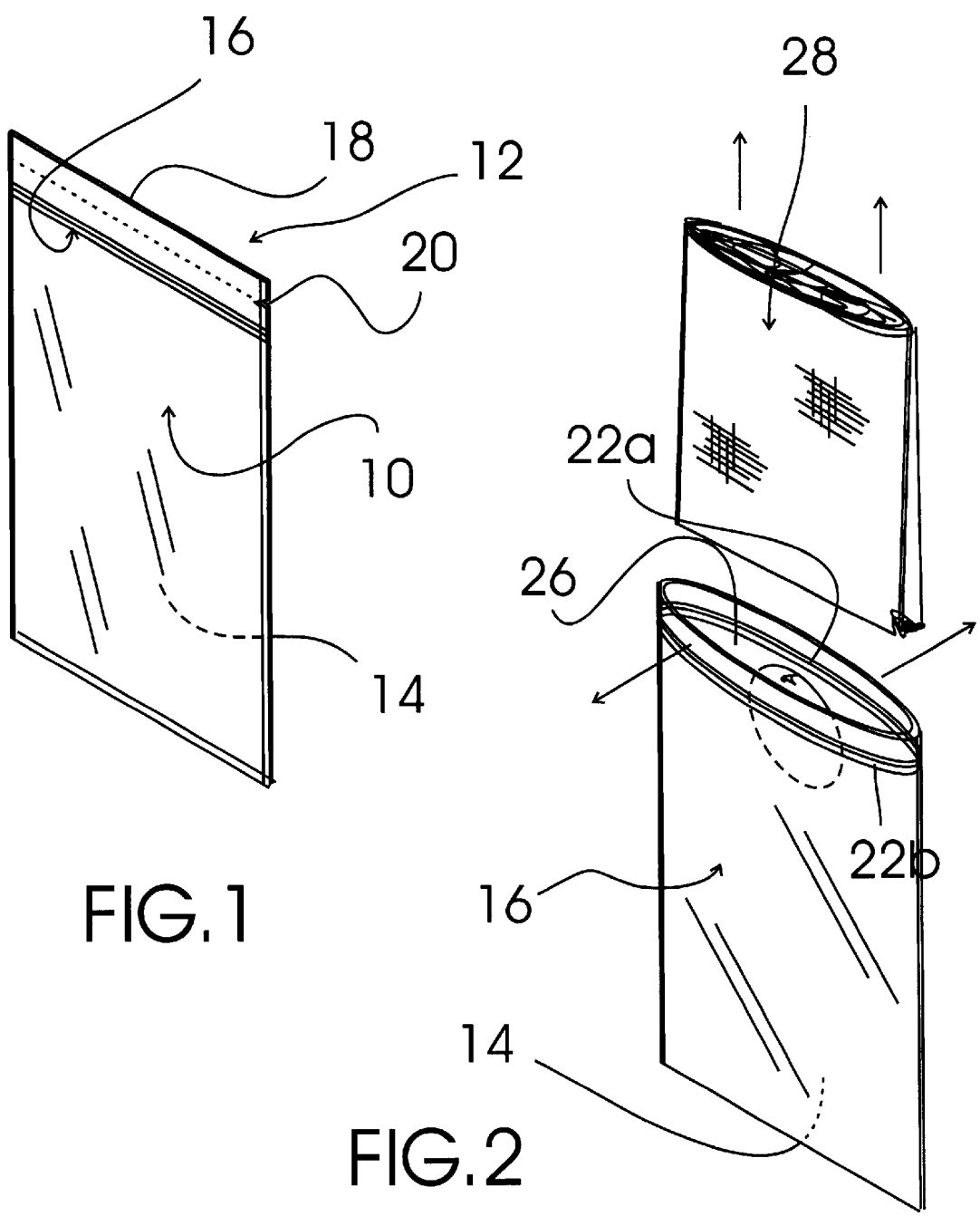

DISPOSABLE PATIENT GARMENT SYSTEM

TECHNICAL FIELD

The present invention relates to disposable patient garments that are discarded after being worn during a medical procedure and more particularly to a disposable patient garment system for use by women undergoing gynecological exams that includes a disposable patient garment constructed of a disposable material in the general shape of elastic waisted shorts that have a split from the front center thereof down between the two legs and up the back side to the back center thereof, and a sealed moisture proof packaging and disposal bag having a sealed lower garment holding chamber within which the disposable patient garment is packaging for shipping and storage; the sealed moisture proof packaging and disposal bag having a plastic outer bag defining the lower garment holding chamber; two trackways attached to the upper edges of the interior sidewalls that define the lower garment holding chamber are interlockable and form the two-parts of the two-part sealing mechanism that is securable together to seal the garment holding chamber prior to disposal of the disposable patient garment; the top edge of the plastic outer bag being heat sealed to package the disposable patient garment; the heat sealed top edge having a tear enablement cut out section located just there below to facilitate tearing off of the heat sealed edge for removal of the disposable patient garment; the interior wall defining the garment holding chamber having a rupturable disinfectant holding cell filled with an alcohol based disinfectant provided thereon; the rupturable holding cell being ruptured after the disposable patient garment is inserted back within the garment holding chamber after use and before sealing the garment holding chamber prior to disposal with the two-part sealing mechanism.

BACKGROUND ART

Many patients, particularly those about to undergo gynecological examinations, feel exposed and vulnerable wearing the traditional wrap around garment typically provided by the health care establishment. It would be a benefit to these individuals to have a disposable patient garment that is constructed in the general shape of elastic waisted shorts that could be worn while waiting to be examined but that had a split from the front center thereof down between the two legs and up the back side to the back center thereof to not hinder the examination. Because the disposable garments are often exposed to bodily fluids and the like during use, they must be disposed of according to stringent health regulations. It would, therefore, be desirable to have a moisture proof packaging and disposal bag that could be used to initially package and store the disposable patient garment and that included a sealable lower garment holding chamber into which the used disposable patient garment could be sealed with a two-part sealing mechanism after a rupturable disinfectant holding cell filled with an alcohol based disinfectant was ruptured to ensure safe disposal of the medical waste.

GENERAL SUMMARY DISCUSSION OF INVENTION

It is thus an object of the invention to provide a disposable patient garment system that includes a disposable patient garment that is constructed in the general shape of elastic waisted shorts that can be worn while waiting to be examined but that have a split from the front center thereof down between the two legs and up the back side to the back center thereof to not hinder the examination.

It is a further object of the invention to provide a disposable patient garment system that includes a moisture proof packaging and disposal bag that is used to initially package and store the disposable patient garment and that includes a sealable lower garment holding chamber into which the used disposable patient garment is sealed with a two-part sealing mechanism after a rupturable disinfectant holding cell filled with an alcohol based disinfectant is ruptured to ensure safe disposal of the medical waste.

It is a still further object of the invention to provide a disposable patient garment system that includes a disposable patient garment constructed of a disposable material in the general shape of elastic waisted shorts that have a split from the front center thereof down between the two legs and up the back side to the back center thereof, and a sealed moisture proof packaging and disposal bag having a sealed lower garment holding chamber within which the disposable patient garment is packaging for shipping and storage; the sealed moisture proof packaging and disposal bag having a plastic outer bag defining the lower garment holding chamber; two trackways attached to the upper edges of the interior sidewalls that define the lower garment holding chamber are interlockable and form the two-parts of the two-part sealing mechanism that is securable together to seal the garment holding chamber prior to disposal of the disposable patient garment; the top edge of the plastic outer bag being heat sealed to package the disposable patient garment; the heat sealed top edge having a tear enablement cut out section located just there below to facilitate tearing off of the heat sealed edge for removal of the disposable patient garment; the interior wall defining the garment holding chamber having a rupturable disinfectant holding cell filled with an alcohol based disinfectant provided thereon; the rupturable holding cell being ruptured after the disposable patient garment is inserted back within the garment holding chamber after use and before sealing the garment holding chamber prior to disposal with the two-part sealing mechanism.

It is a still further object of the invention to provide a disposable patient garment system that accomplishes all or some of the above objects in combination.

Accordingly, a disposable patient garment system is provided. The disposable patient garment system includes a disposable patient garment constructed of a disposable material in the general shape of elastic waisted shorts that have a split from the front center thereof down between the two legs and up the back side to the back center thereof, and a sealed moisture proof packaging and disposal bag having a sealed lower garment holding chamber within which the disposable patient garment is packaging for shipping and storage; the sealed moisture proof packaging and disposal bag having a plastic outer bag defining the lower garment holding chamber; two trackways attached to the upper edges of the interior sidewalls that define the lower garment holding chamber are interlockable and form the two-parts of the two-part sealing mechanism that is securable together to seal the garment holding chamber prior to disposal of the disposable patient garment; the top edge of the plastic outer bag being heat sealed to package the disposable patient garment; the heat sealed top edge having a tear enablement cut out section located just there below to facilitate tearing off of the heat sealed edge for removal of the disposable patient garment; the interior wall defining the garment holding chamber having a rupturable disinfectant holding cell filled with an alcohol based disinfectant provided thereon; the rupturable holding cell being ruptured after the disposable patient garment is inserted back within the garment holding chamber after use and before sealing the garment holding chamber prior to disposal with the two-part sealing mechanism.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is a perspective view of an exemplary embodiment of the sealed moisture proof packaging and disposal bag of the disposable patient garment system of the present invention showing the sealed lower garment holding chamber, the trackways of the two-part sealing mechanism secured together sealing the garment holding chamber, and the heat sealed top edge with the tear enablement cut out section.

FIG. 2 is an exploded perspective view of the disposable patient garment system of FIG. 1 with the heat sealed top edge torn away, the trackways of the two-part sealing mechanism disconnected to reveal the garment holding chamber, the rupturable disinfectant holding cell formed on an interior wall of the packaging and disposal unit, and the disposable patient garment lifted out of the garment holding chamber through the access opening defined between the trackways of the two-part sealing mechanism.

EXEMPLARY MODE FOR CARRYING OUT THE INVENTION

Figure 3:
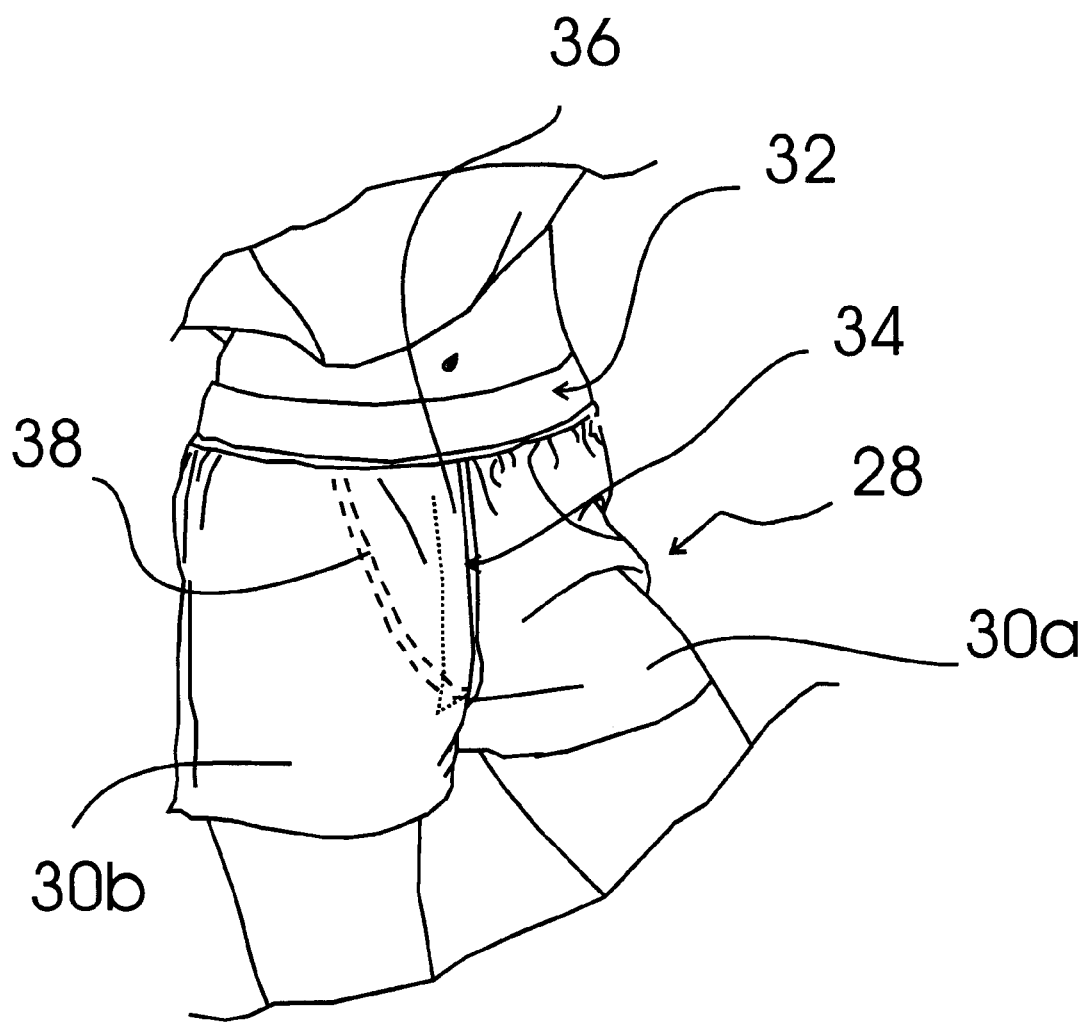
FIG. 3 is a perspective view showing the disposable patient garment constructed of a disposable material in the general shape of elastic waisted shorts and having a split from the front center thereof down between the two legs and up the back side to the back center thereof.
Figure 4:
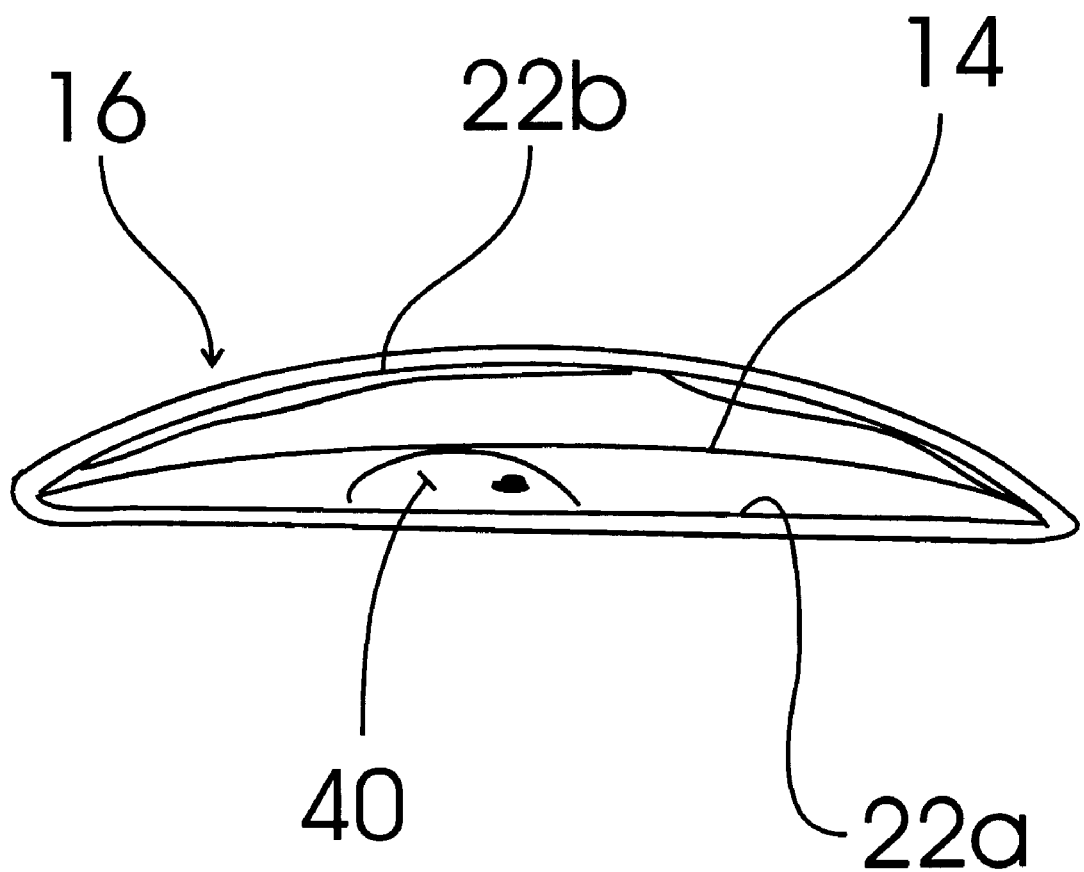
FIG. 4 is a top plan view showing the access opening into the garment holding chamber, the rupturable disinfectant holding cell filled with an alcohol based disinfectant, and the trackways of the two-part sealing mechanism disconnected.

FIG. 1 shows an exemplary embodiment of the sealed moisture proof packaging and disposal bag, generally designated 10, of the disposable patient garment system, generally designated 12, of the present invention. Sealed moisture proof packaging and disposal bag 10 has a lower garment holding chamber formed therein 14; a two-part sealing mechanism, generally designated 16; and a heat sealed top edge 18 with a tear enablement cut out section 20 provided to ease tearing off of heat sealed top edge 18 when opening bag 10.

Referring to FIG. 2, With heat sealed top edge 18 discarded, the interlockable trackways 22a,22b of two-part sealing mechanism 16 are disconnected to provide an access opening 26 through which a disposable patient garment, generally designated 28 is removed from garment holding chamber 14 where it is positioned during packaging.

Referring now to FIG. 3, disposable patient garment 28 is constructed of a disposable paper material in the general shape of shorts having two legs 30a,30b; an elastic waist band 32; and a split, generally designated 34, running from the front center 36 of shorts 28 down between the two legs 30a,30b and up the back side of shorts 28 to the back center 38 thereof.

After use, disposable patient garment 28 is folded and inserted into garment holding chamber 14; a rupturable disinfectant holding cell 40 formed on an interior wall defining garment holding chamber 14 and filled with an alcohol based disinfectant is ruptured; and the two trackways 22a,22b of the two-part sealing mechanism 16 are sneezed together sealing garment holding chamber 14 for safe disposal.

It can be seen from the preceding description that a disposable patient garment system has been provided that includes a disposable patient garment that is constructed in the general shape of elastic waisted shorts that can be worn while waiting to be examined but that have a split from the front center thereof down between the two legs and up the back side to the back center thereof to not hinder the examination; that includes a moisture proof packaging and disposal bag that is used to initially package and store the disposable patient garment and that includes a sealable lower garment holding chamber into which the used disposable patient garment is sealed with a two-part sealing mechanism after a rupturable disinfectant holding cell filled with an alcohol based disinfectant is ruptured to ensure safe disposal of the medical waste; and that includes a disposable patient garment constructed of a disposable material in the general shape of elastic waisted shorts that have a split from the front center thereof down between the two legs and up the back side to the back center thereof, and a sealed moisture proof packaging and disposal bag having a sealed lower garment holding chamber within which the disposable patient garment is packaging for shipping and storage; the sealed moisture proof packaging and disposal bag having a plastic outer bag defining the lower garment holding chamber; two trackways attached to the upper edges of the interior sidewalls that define the lower garment holding chamber are interlockable and form the two-parts of the two-part sealing mechanism that is securable together to seal the garment holding chamber prior to disposal of the disposable patient garment; the top edge of the plastic outer bag being heat sealed to package the disposable patient garment; the heat sealed top edge having a tear enablement cut out section located just there below to facilitate tearing off of the heat sealed edge for removal of the disposable patient garment; the interior wall defining the garment holding chamber having a rupturable disinfectant holding cell filled with an alcohol based disinfectant provided thereon; the rupturable holding cell being ruptured after the disposable patient garment is inserted back within the garment holding chamber after use and before sealing the garment holding chamber prior to disposal with the two-part sealing mechanism.

It is noted that the embodiment of the disposable patient garment system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A disposable patient garment system comprising:

a disposable patient garment constructed of a disposable material into elastic waisted shorts that have a split from a front center thereof down between two legs thereof and up a back side to a back center thereof; and a sealed moisture proof packaging and disposal bag having a sealed lower garment holding chamber within which said disposable patient garment is packaging for shipping and storage;

said sealed moisture proof packaging and disposal bag having a plastic outer bag defining said lower garment holding chamber;

two trackways attached to said upper edges of said interior sidewalls that define said lower garment holding chamber are interlockable and form said two-parts of said two-part sealing mechanism that is securable together to seal said garment holding chamber prior to disposal of said disposable patient garment;

said top edge of said plastic outer bag being heat sealed to package said disposable patient garment;

said heat sealed top edge having a tear enablement cut out section located just there below to facilitate tearing off of said heat sealed edge for removal of said disposable patient garment;

said interior wall defining said garment holding chamber having a rupturable disinfectant holding cell filled with an alcohol based disinfectant provided thereon;

said rupturable holding cell being ruptured after said disposable patient garment is inserted back within said garment holding chamber after use and before sealing said garment holding chamber prior to disposal with said two-part sealing mechanism.

* * * * *